United States Patent
Mihashi et al.

(10) Patent No.: US 7,309,126 B2
(45) Date of Patent: Dec. 18, 2007

(54) EYE CHARACTERISTICS MEASURING DEVICE

(75) Inventors: Toshifumi Mihashi, Tokyo (JP); Yoko Hirohara, Tokyo (JP); Naoyuki Maeda, Osaka (JP)

(73) Assignee: Kabushiki Kaisha Topcon, Tokyo (JP)

( * ) Notice: Subject to any disclaimer, the term of this patent is extended or adjusted under 35 U.S.C. 154(b) by 416 days.

(21) Appl. No.: 10/399,611

(22) PCT Filed: Oct. 16, 2001

(86) PCT No.: PCT/JP01/09083

§ 371 (c)(1),
(2), (4) Date: Apr. 18, 2003

(87) PCT Pub. No.: WO02/32298

PCT Pub. Date: Apr. 25, 2002

(65) Prior Publication Data

US 2004/0012760 A1 Jan. 22, 2004

(30) Foreign Application Priority Data

Oct. 18, 2000 (JP) ............................ 2000-318534

(51) Int. Cl.
*A61B 3/10* (2006.01)
*A61B 3/00* (2006.01)
(52) U.S. Cl. ................. 351/205; 351/200; 351/211; 351/212; 351/247; 351/221; 606/4; 606/5
(58) Field of Classification Search ................ 351/205, 351/206, 208, 211, 212, 221, 200, 215, 216, 351/246, 247; 606/4, 5, 10; 345/700, 761, 345/764
See application file for complete search history.

(56) References Cited

U.S. PATENT DOCUMENTS

| | | | | | |
|---|---|---|---|---|---|
| 4,678,297 | A | * | 7/1987 | Ishikawa et al. | 351/208 |
| 4,878,750 | A | * | 11/1989 | Sekiguchi | 351/212 |
| 5,011,276 | A | * | 4/1991 | Iwamoto | 351/211 |
| 5,214,456 | A | * | 5/1993 | Gersten | 351/212 |
| 5,291,560 | A | * | 3/1994 | Daugman | 382/117 |
| 5,327,191 | A | * | 7/1994 | Shindo et al. | 396/51 |
| 5,357,294 | A | * | 10/1994 | Shimizu et al. | 351/212 |
| 5,500,697 | A | * | 3/1996 | Fujieda | 351/212 |
| 5,557,350 | A | * | 9/1996 | Yano | 351/208 |

(Continued)

FOREIGN PATENT DOCUMENTS

EP 0 947 158 A1 10/1999

(Continued)

OTHER PUBLICATIONS

U.S. Appl. No. 10/399,612, filed Apr. 18, 2003, Mihashi et al.

*Primary Examiner*—Loha Ben
(74) *Attorney, Agent, or Firm*—Foley & Lardner LLP

(57) ABSTRACT

A device for measuring eye characteristics, an operation device, and the coordinate origin and the coordinate axes of each eye are sufficiently related with one another. A measuring unit (111) measures eye optical characteristics based on a first light receiving signal from a first light receiving unit (23), and measures a cornea topography based on a second light receiving signal from a second light receiving unit (35). The measuring unit (111) also computes an ablation amount based on an aberration result.

15 Claims, 12 Drawing Sheets

U.S. PATENT DOCUMENTS

| | | | |
|---|---|---|---|
| 5,684,562 A * | 11/1997 | Fujieda | 351/212 |
| 5,757,461 A * | 5/1998 | Kasahara et al. | 351/206 |
| 5,865,832 A * | 2/1999 | Knopp et al. | 606/10 |
| 6,053,614 A * | 4/2000 | Kawamura et al. | 351/211 |
| 6,070,981 A | 6/2000 | Mihashi et al. | |
| 6,193,371 B1 * | 2/2001 | Snook | 351/212 |
| 6,234,631 B1 * | 5/2001 | Sarver et al. | 351/212 |
| 6,382,796 B1 * | 5/2002 | Ban | 351/212 |
| 6,467,907 B1 * | 10/2002 | Fujieda et al. | 351/212 |
| 6,588,902 B2 * | 7/2003 | Isogai | 351/208 |
| 6,905,209 B2 * | 6/2005 | Mihashi et al. | 351/221 |
| 6,932,475 B2 * | 8/2005 | Molebny et al. | 351/215 |

FOREIGN PATENT DOCUMENTS

| | | |
|---|---|---|
| JP | 3-51166 B3 | 8/1991 |
| JP | 6-189905 A | 7/1994 |
| JP | 8-164113 A | 6/1996 |
| JP | 2706251 B2 | 10/1997 |
| JP | 10-216092 A | 8/1998 |
| JP | 10-305013 A | 11/1998 |
| JP | 11-028188 A | 2/1999 |
| JP | 11-137520 A | 5/1999 |
| JP | 11-137522 A | 5/1999 |
| JP | 11-276437 A | 10/1999 |
| JP | 11-342152 A | 12/1999 |

* cited by examiner

EYE CHARACTERISTICS MEASURING DEVICE

BACKGROUND OF THE INVENTION

The present invention relates to an eye characteristic measuring apparatus, and particularly to an eye characteristic measuring apparatus which measures the optical characteristics of an eye, and relates those with a predetermined coordinate system of the eye to be examined or displays those.

In recent years, the variety of optical instruments used for medicine is very wide. Especially in ophthalmology, this optical instrument is in widespread use as an optical characteristic measuring apparatus for examining ocular functions such as ocular refraction or adjustment, and the inside of an eyeball. With respect to measurement results of these various tests, it is important that a patient's eye to be measured as a test object is placed under what measurement conditions. For example, since the pupil of an eye becomes small in a bright place, and becomes large in a dark place, it is necessary to also consider luminous intensity as the measurement condition, and further, a measurement range of the eye to be measured is also important.

Besides, the shapes of a retina, a cornea and other parts of an eye are often peculiar to a patient, and in order for an eye doctor or the like to quickly perform diagnosis of the patient's eye to be measured, it is desirable that various data relating to the respective parts of the eye to be measured are collectively displayed or desired data are selected and displayed. By this, the eye doctor or the like can intelligibly explain various diagnoses (observations) to the patient.

In general, cornea topography is effective for many uses, for example, an estimate of result of an operation such as keratotomy or keratectomy, clinical test after corneal transplant, design and evaluation of a contact lens for myopia/hyperopia, and diagnosis/disease judgment of a cornea. As a conventional method of measuring the corneal shape, there is, for example, a placido disk technique, a stereogram technique, a moire technique, a topography interferometric technique or the like.

SUMMARY OF THE INVENTION

However, in a conventional eye characteristic measuring apparatus, a processing is performed such that the coordinate of the measuring apparatus itself, for example, the center of a light receiving section is made the coordinate origin. Thus, according to such a coordinate system, there is a case where the measurement data is not sufficiently related with the eye, and it is not necessarily adequate.

In view of the above, an object of the invention is to provide an eye characteristic measuring apparatus in which the measuring apparatus of eye characteristics, an operation apparatus, and a coordinate origin and coordinate axes of each eye are sufficiently related with one another.

Besides, another object of the invention is to perform the relating with the coordinate axes with respect to rotational eye movement and transfer eye movement as well. Further, another object of the invention is to enable handling in accordance with motion of the eye.

According to first solving means of the invention, an eye characteristic measuring apparatus comprises a first illumination optical system including a first light source section for emitting a first light flux of a first wavelength and for illuminating an eyeground to be examined with the first light flux from the first light source section, a first light receiving optical system including a first light receiving section for forming a first received light signal from a received light flux and for guiding a light flux reflected and returned from the eyeground to be examined to the first light receiving section, a second light receiving optical system including a second light receiving section for forming a second received light signal including information of an anterior eye part from a received light flux and for guiding a second light flux including information relating to a feature portion of the anterior eye part of the eye to be examined to the second light receiving section, a measurement section for obtaining optical characteristics including refractive power of the eye to be examined based on the first received light signal from the first light receiving section, a coordinate setting section for forming a coordinate system based on feature signals included in the second received light signal and corresponding to an image of the feature portion of the anterior eye part of the eye to be examined, and a display section for displaying the optical characteristics of the eye to be examined obtained by the measurement section in relation to the coordinate system formed by the coordinate setting section.

According to second solving means of the invention, an eye characteristic measuring apparatus comprises a second illumination optical system for applying an illumination pattern for detection of a feature portion of an anterior eye part of an eye to be examined, a second light receiving optical system including a second light receiving section for forming a second received light signal from a received light flux and for guiding a light flux reflected and returned from the eye to be examined to the second light receiving section, a measurement section for obtaining optical characteristics including a cornea shape of the eye to be examined based on the second received light signal from the second light receiving section, a coordinate setting section for forming a coordinate system based on feature signals included in the second received light signal and corresponding to an image of the feature portion of the anterior part of the eye to be examined, and a display section for displaying the optical characteristics of the eye to be examined obtained by the measurement section in relation to the coordinate system formed by the coordinate setting section.

According to third solving means of the invention, an eye characteristic measuring apparatus comprises a first illumination optical system including a first light source section for emitting a first light flux of a first wavelength and for illuminating an eyeground to be examined with the first light flux from the first light source section, a first light receiving optical system including a first light receiving section for forming a first received light signal from a received light flux and for guiding a light flux reflected and returned from the eyeground to be examined to the first light receiving section, a second light receiving optical system including a second light receiving section for forming a second received light signal including information of an anterior part from a received light flux and for guiding a second light flux including information relating to a marker formed at the anterior part of the eye to be examined to the second light receiving section, a measurement section for obtaining optical characteristics including refractive power of the eye to be examined based on the first received light signal from the first light receiving section, a coordinate setting section for forming a coordinate system based on a marker signal concerning the marker provided at the eye to be examined and feature signals corresponding to an image of the feature portion of the anterior part of the eye to be examined, which are included in the second received light signal, and a display section for displaying the optical characteristics of the eye to be examined obtained by the measurement section in relation to the coordinate system formed by the coordinate setting section.

According to fourth solving means of the invention, an eye characteristic measuring apparatus comprises a second illumination optical system having a pattern for detection of a feature portion of an anterior part of an eye to be examined and for illuminating the eye to be examined provided with a mark, a second light receiving optical system including a second light receiving section for forming a second received light signal from a received light flux and for guiding a light flux reflected and returned from the eye to be examined to the second light receiving section, a measurement section for obtaining optical characteristics including a corneal shape of the eye to be examined based on the second received light signal from the second light receiving section, a coordinate setting section for forming a coordinate system based on a marker signal of the marker provided at the eye to be examined and feature signals corresponding to an image of the feature portion of the anterior part of the eye to be examined, which are included in the second received light signal, and a display section for displaying the optical characteristics of the eye to be examined obtained by the measurement section in relation to the coordinate system formed by the coordinate setting section.

DETAILED DESCRIPTION OF THE PREFERRED EMBODIMENTS

Figure 1:
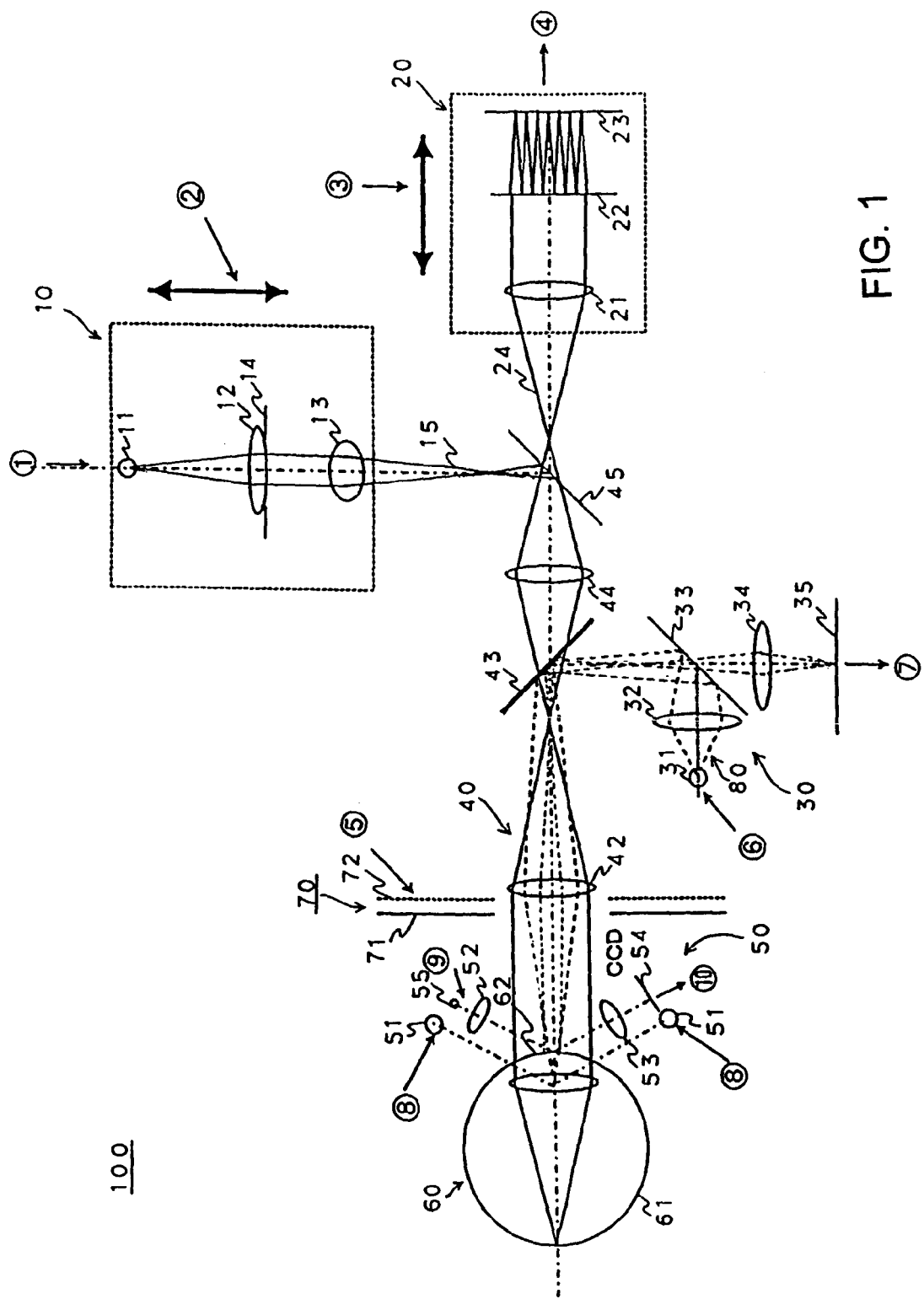
FIG. 1 is a view showing a schematic optical system of an eye characteristic measuring apparatus of the invention.

FIG. 1 is a view schematically showing an optical system 100 of an eye optical characteristic measuring apparatus of the invention.

The optical system 100 of the eye optical characteristic measuring apparatus is, for example, an apparatus for measuring the optical characteristics of an eye 60 to be measured as an object, and includes a first illumination optical system 10, a first light receiving optical system 20, a second light receiving optical system 30, a common optical system 40, an adjusting optical system 50, a second illumination optical system 70, and a second light sending optical system 80. Incidentally, with respect to the eye 60 to be measured, a retina 61 and a cornea 62 are shown in the drawing.

The first illumination optical system 10 includes, for example, a first light source section 11 for emitting a light flux of a first wavelength, and a condensing lens 12, and is for illuminating a minute region on the retina (eyeground) 61 of the eye 60 to be measured by the light flux from the first light source section 11 so that the illumination conditions can be suitably set. Incidentally, here, as an example, the first wavelength of the light flux for illumination emitted from the first light source section 11 is a wavelength of an infrared range (for example, 840 nm, 780 nm, etc.).

It is desirable that the first light source section 11 has a large spatial coherence and a small temporal coherence. Here, the first light source section 11 is, for example, a super luminescence diode (SLD), and a point light source having high luminance can be obtained. Incidentally, the first light source section 11 is not limited to the SLD, and for example, even a laser having a large spatial coherence and temporal coherence can be used by inserting a rotational diffusion plate to suitably lower the temporal coherence. Further, even an LED having a small spatial coherence and temporal coherence can be used by, if light quantity is sufficient, inserting a pinhole or the like at the position of a light source of a light path.

The first light receiving optical system 20 includes, for example, a collimating lens 21, a Hartmann plate 22 as a conversion member for converting a part of a light flux (first light flux) reflected and returned from the retina 61 of the eye 60 to be measured into at least 17 beams, and a first light receiving section 23 for receiving the plural beams converted by the Hartmann plate 22, and is for guiding the first light flux to the first light receiving section 23. Here, a CCD with low lead-out noise is adopted for the first light receiving section 23, and as the CCD, a suitable type one, for example, a general low noise type one or a cooling CCD of 1000*1000 elements for measurement can be applied.

Figure 2:
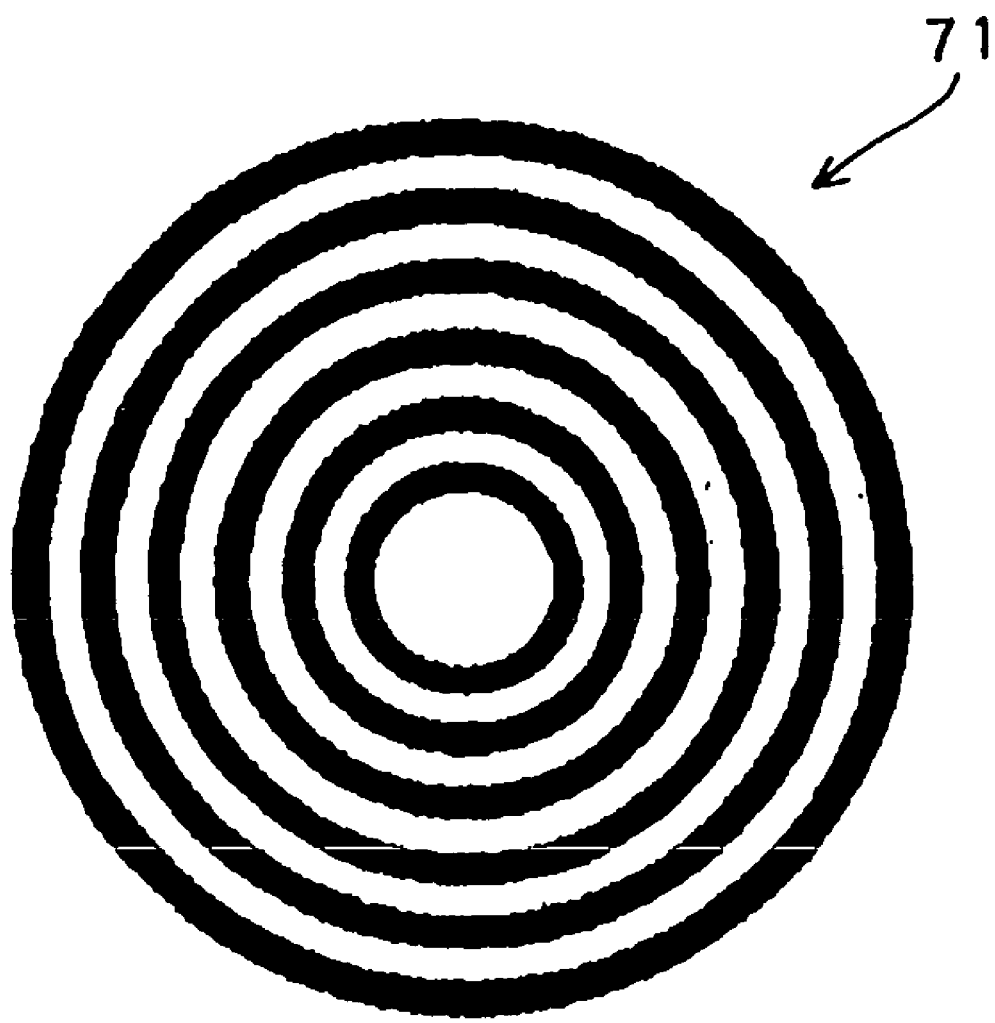
FIG. 2 is an electric block diagram showing an electric structure of the eye characteristic measuring apparatus of the invention.

The second illumination optical system 70 includes a second light source 72 and a placido's disc 71. Incidentally, the second light source 72 can be omitted. FIG. 2 shows an example of a structural view of the placido's disc. The placido's disc 71 is for projecting an index of a pattern made of plural co-axial rings. Incidentally, the index of the pattern made of the plural co-axial rings is an example of indexes of predetermined patterns, and another suitable pattern can be used. After alignment adjustment described later is completed, the index of the pattern made of the plural co-axial rings can be projected.

The second light sending optical system 80 is for mainly performing, for example, after-mentioned alignment adjustment, and measurement and adjustment of a coordinate origin and a coordinate axis, and includes a second light source section 31 for emitting a light flux of a second wavelength, a light condensing lens 32, and a beam splitter 33.

The second light receiving optical system 30 includes a condensing lens 34, and a second light receiving section 35. The second light receiving optical system 30 guides a light flux (second light flux) of the pattern of the placido's disc 71 illuminated from the second illumination optical system 70, and reflected and returned from the anterior eye part or the cornea 62 of the eye 60 to be measured, toward the second light receiving section 35. Besides, it can also guide a light flux emitted from the second light source 31, and reflected and returned from the cornea 62 of the eye 60 to be measured, toward the second light receiving section 35. Incidentally, the second wavelength of the light flux emitted from the second light source section 31 is different from, for example, the first wavelength (here, 780 nm), and a wavelength (for example, 940 nm) longer than that can be selected.

The common optical system 40 is disposed on the optical axis of the light flux emitted from the first illumination optical system 10, and can be included in common in the first and second illumination optical systems 10 and 70, the first and second light receiving optical systems 20 and 30, and the second light sending optical system 80. The common optical system includes, for example, an afocal lens 42, beam splitters 43 and 45, and a condensing lens 44. The beam splitter 43 is formed of such a mirror (for example, a dichroic mirror) that the wavelength of the second light source section 31 is sent (reflected) to the eye 60 to be measured, and the second light flux reflected and returned from the retina 61 of the eye 60 to be measured is reflected, whereas the wavelength of the first light source 11 is transmitted. The beam splitter 45 is formed of such a mirror (for example, dichroic mirror) that the wavelength of the first light source section 11 is sent (reflected) to the eye 60 to be measured, and the first light flux reflected and returned from the retina 61 of the eye 60 to be measured is transmitted. The beam splitters 43 and 45 prevent the first and the second light fluxes from entering different optical systems and generating noise.

The adjusting optical system 50 mainly performs, for example, a working distance adjustment described later, and includes a third light source section 51, a fourth light source section 55, condensing lenses 52 and 53, and a third light receiving section 54.

Next, the alignment adjustment will be described. The alignment adjustment is mainly carried out by the second light receiving optical system 30 and the second light sending optical system 80.

First, the light flux from the second light source section 31 illuminates the eye 60 to be measured as the object with the substantially parallel light flux through the condensing lens 32, the beam splitters 33 and 43, and the afocal lens 42. The reflected light flux reflected by the cornea 62 of the eye 60 to be measured is emitted as a divergent light flux as if it is emitted from a point of ½ of the radius of curvature of the cornea 62. This divergent light source is received as a spot image by the second light receiving section 35 through the afocal lens 42, the beam splitters 43 and 33, and the condensing lens 34.

Here, in the case where the spot image on the second light receiving section 35 is deviated from the light axis, the body of the eye optical characteristic measuring apparatus is moved and adjusted vertically and horizontally to make the spot image coincident with the light axis. When the spot image coincides with the optical axis in this way, the alignment adjustment is completed. Incidentally, when the cornea 62 of the eye 60 to be measured is illuminated with a third light source section 51, an image of the eye 60 to be measured obtained by this illumination is formed on the second light receiving section 35, and accordingly, the alignment adjustment may be made such that this image is used to make the pupil center coincident with the optical axis.

Next, the working distance adjustment will be described. The working distance adjustment is carried out mainly by the adjusting optical system 50.

First, the working distance adjustment is carried out in such a manner that the parallel light flux in the vicinity of the optical axis emitted from the fourth light source section 55 is illuminated to the eye 60 to be measured, and the light reflected from this eye 60 to be measured is received by the third light receiving section 54 through the condensing lenses 52 and 53. In the case where the eye 60 to be measured is within a suitable working distance, a spot image from the fourth light source section 55 is formed on the optical axis of the third light receiving section 54. On the other hand, in the case where the eye 60 to be measured is outside the suitable working distance in front and rear, the spot image from the fourth light source 55 is formed above or below the optical axis of the third light receiving section 54. Incidentally, since it is sufficient if the third light receiving section 54 can detect the change of the light flux position on the plane including the fourth light source section 55, the optical axis, and the third light receiving section 54, for example, a one-dimensional CCD disposed on this plane, a position sensing device (PSD) or the like can be applied.

Next, the positional relation between the first illumination optical system 10 and the first light receiving optical system 20 will be roughly described.

The beam splitter 45 is inserted in the first light receiving optical system 20, and by this beam splitter 45, the light from the first illumination optical system 10 is sent to the eye 60 to be measured, and the reflected light from the eye 60 to be measured is transmitted. The first light receiving section 23 included in the first light receiving optical system 20 receives the light transmitted through the Hartmann plate 22 as the conversion member and generates a received light signal.

The first light source section 11 and the retina 61 of the eye 60 to be measured form a conjugate relation. The retina 61 of the eye 60 to be measured and the first light receiving section 23 are conjugate with each other. The Hartmann plate 22 and the pupil of the eye 60 to be measured form a conjugate relation. The first light receiving optical system 20, the cornea 62 and pupil of the eye 60 to be measured, and Hartmann plate 22 form a substantially conjugate relation. That is, the front side focus of the afocal lens 42 is substantially coincident with the cornea 62 and the pupil of the eye 60 to be measured.

The first illumination optical system 10 and the first light receiving optical system 20 are moved together so that on the assumption that the light flux from the first light source 11 is reflected at the condensed point, a signal peak by the reflected light at the first light receiving section 23 becomes maximum. Specifically, the first illumination optical system 10 and the first light receiving optical system 20 move in the direction that the signal peak at the first light receiving section 23 becomes large, and stop at the position where the signal peak becomes maximum. By this, the light flux from the first light source section 11 is condensed on the eye 60 to be measured.

The lens 12 converts the diffused light of the light source 11 into parallel light. A diaphragm 14 is put at a position optically conjugate with the pupil of the eye or the Hartmann plate 22. In the diaphragm 14, its diameter is smaller than the effective range of the Hartmann plate 22, and so-called single path aberration measurement (a method in which aberration of an eye influences only the light receiving side) is established. A lens 13 is disposed such that an eyeground conjugate point of a real light beam is at the front side focal position to satisfy the above, and further, the rear side focal position is coincident with the diaphragm 14 to satisfy the conjugate relation to the pupil of the eye.

After a light beam 15 comes to have an optical path common to a light beam 24 by the beam splitter 45, it approximately advances in the same way as the light beam 24. At the time of single path measurement, the diameters of the respective light beams are different from each other, and the beam diameter of the light beam 15 is set to be rather thinner than the light beam 24. Specifically, the beam diameter of the light beam 15 is, for example, about 1 mm at the position of the pupil of the eye, and the beam diameter of the light beam 24 becomes about 7 mm (incidentally, in the drawing, the light beam 15 from the beam splitter 45 to the eyeground 61 is omitted.

Next, the Hartmann plate 22 as the conversion member will be described.

The Hartmann plate 22 included in the first light receiving optical system 20 is a wavefront conversion member for converting a reflected light flux into plural beams. Here, plural micro Fresnel lenses disposed in the plane orthogonal to the optical axis are applied for the Hartmann plate 22. In general, with respect to a measurement object (the eye 60 to be measured), in order to measure a spherical component of the eye 60 to be measured, third astigmatism, and the other higher order aberration, it is necessary to make a measurement with at least 17 beams through the eye 60 to be measured.

The micro Fresnel lens is an optical element, and includes, for example, rings of height pitch for each wavelength and blades optimized for emission parallel with condensing point. The micro Fresnel lens here is provided with light path length differences of eight levels in which a semiconductor minute working technique is applied, and achieves a high condensing rate (for example, 98%).

The reflected light from the retina 61 of the eye 60 to be measured passes through the afocal lens 42 and the collimate lens 21, and is condensed onto the first light receiving section 23 through the Hartmann plate 22. Accordingly, the Hartmann plate 22 includes the wavefront conversion member for converting the reflected light flux into at least 17 beams.

Figure 3:
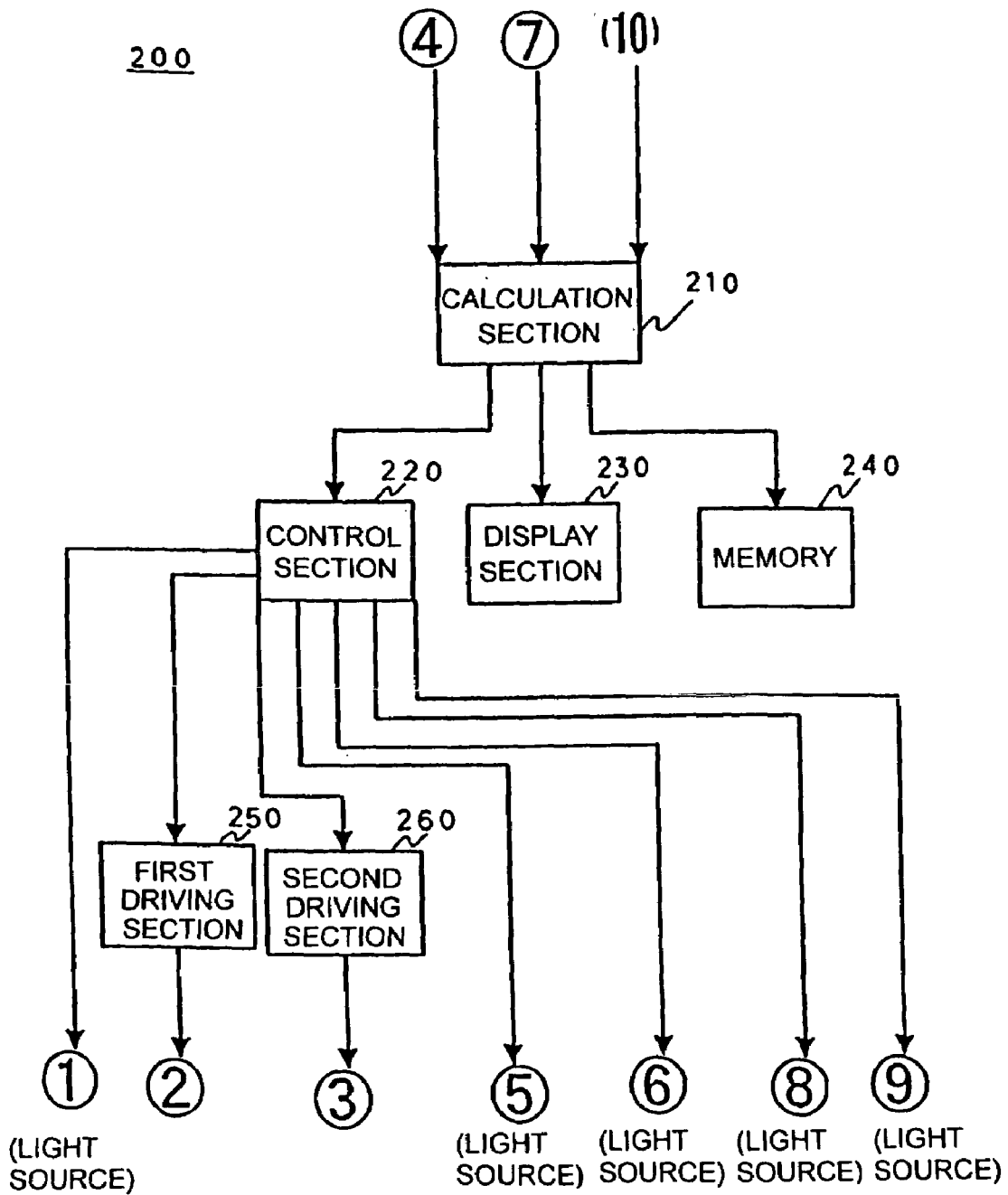
FIG. 3 is a flowchart of the eye characteristic measuring apparatus of the invention.

FIG. 3 is a block diagram schematically showing an electric system 200 of the eye optical characteristic measuring apparatus of the invention. The electric system 200 of the eye optical characteristic measuring apparatus includes, for example, a calculation section 210, a control section 220, a display section 230, a memory 240, a first driving section 250, and a second driving section 260.

The calculation section 210 receives a received light signal (first signal) ④ obtained from the first light receiving section 23, a received light signal (second signal) ⑦ obtained from the second light receiving section 35, and a received light signal ⑩ obtained from the third light receiving section 54, and calculates a coordinate origin, a coordinate axis, movement of a coordinate, rotation, ocular aberration, corneal aberration, Zernike coefficients, aberration coefficients, Strehl ratio, white light MTF, Landolt's ring pattern, and the like. Further, the calculation section outputs signals corresponding to the calculation results to the control section 220 for controlling the whole of the electric driving system, the display section 230, and the memory 240. The details of the calculation section 210 are described later.

The control section 220 controls switching on and off of the first light source section 11 on the basis of the control signal from the calculation section 210, and controls the first driving section 250 and the second driving section 260. For example, on the basis of the signal corresponding to the calculation result in the calculation section 210, the control section outputs a signal ① to the first light source section 11, outputs a signal ⑤ to the placido's disc 71, outputs a signal ⑥ to the second light source section 31, outputs a signal ⑧ to the third light source section 51, outputs a signal ⑨ to the fourth light source section 55, and outputs signals to the first driving section 250 and the second driving section 260.

The first driving section 250 moves to the optical axis direction, for example, the whole of the first illumination optical system 10 on the basis of the received light signal ④ inputted to the calculation section 210 from the first light receiving section 23, outputs a signal ② to a not-shown suitable lens moving unit, and drives the lens moving unit. By this, the first driving section 250 can move and-adjust the first illumination optical system 10.

The second driving section 260 moves to the optical axis direction, for example, the whole of the first light receiving optical system 20 on the basis of the received light signal ④ inputted to the calculation section 210 from the first light receiving section 23, and outputs a signal ③ to the not-shown suitable lens moving unit, and drives the lens moving unit. By this, the second driving section 260 can move and adjust the first light receiving optical system 20.

Figure 4:
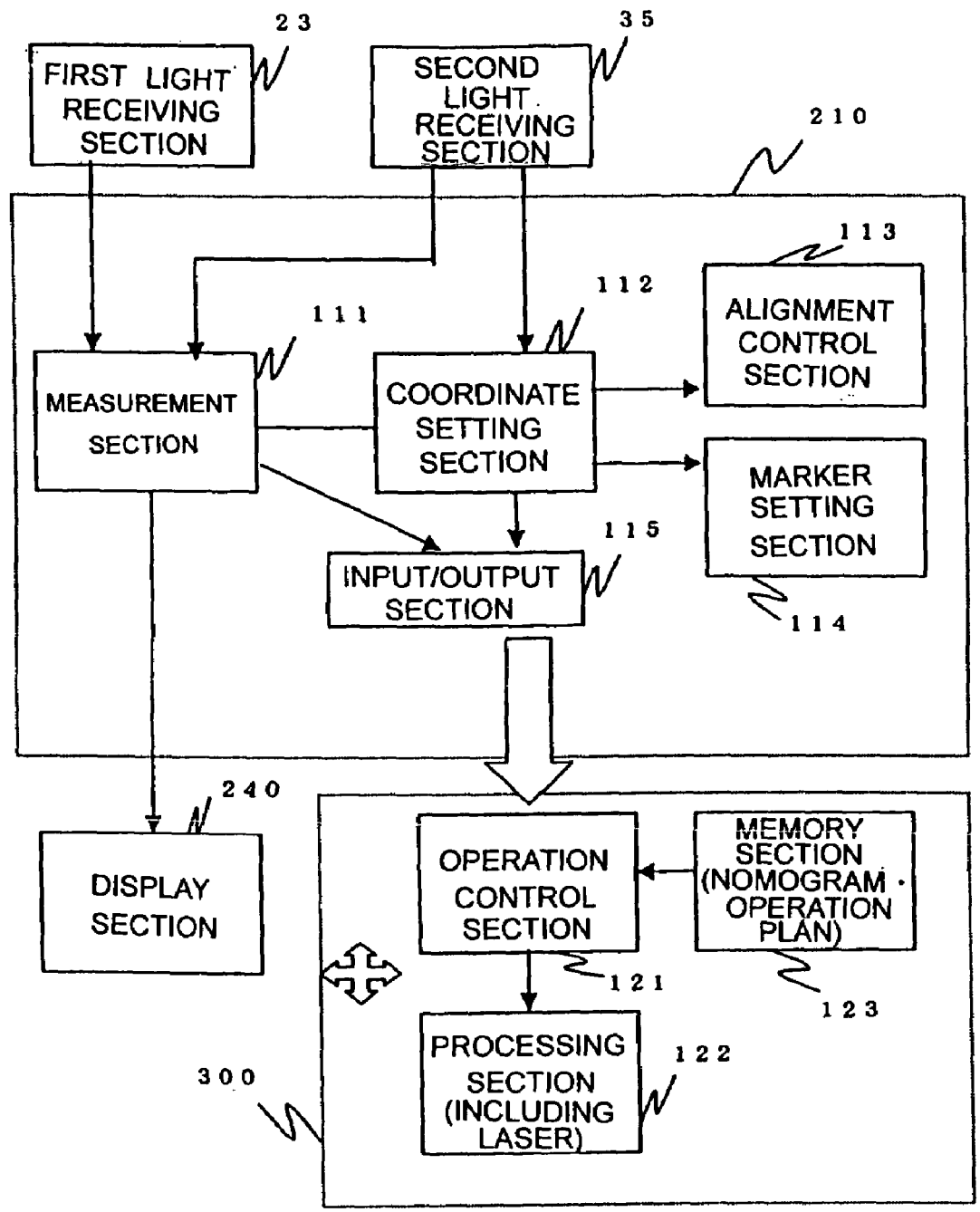
FIG. 4 is a detailed structural view relating to a calculation section of the eye characteristic measuring apparatus of the invention.

FIG. 4 is a detailed structural view of the calculation section of the eye characteristic measuring apparatus of the invention. The calculation section 210 includes a measurement section 111, a coordinate setting section 112, an alignment control section 113, a marker setting section 114, and an input/output section 115.

The first light receiving section 23 forms a first received light signal from the received light flux reflected and returned from the eyeground of the subject eye. The second light receiving section 35 forms a second received light signal including information of the anterior eye part from the received light flux including the feature portion of the anterior part of the subject eye and/or information relating to the marker formed in the anterior part of the subject eye, and guides it to the measurement section 111 and the coordinate setting section 112.

The measurement section 111 obtains the refractivity of the subject eye or the optical characteristics including the corneal shape on the basis of the first received light signal from the first light receiving section 23. The measurement section 111 makes a measurement of ophthalmic optical characteristics especially on the basis of the first received light signal from the first light receiving section 23. Besides, the measurement section 111 makes a corneal shape measurement such as a cornea topography measurement especially on the basis of the second received light signal from the second light receiving section 35. The measurement section 111 calculates an aberration result, and if necessary, an aberration amount, and outputs the calculation result through the input/output section 115 to an operating apparatus.

Besides, the coordinate setting section 112 decides the coordinate origin and the direction of the coordinate axis on the basis of the second received light signal including the feature signal of the anterior part of the subject eye. Besides, the coordinate setting section 112 obtains the coordinate origin, and the rotational and transfer movement of the coordinate axis on the basis of at least one of the feature signals of the anterior part of the subject eye in the second received light signal, and correlates the measurement data with the coordinate axis. Incidentally, the feature part includes at least one of pupil position, pupil center, vertex normal, iris position, iris pattern, shape of the pupil, and limbus shape. For example, the coordinate setting section 112 sets the coordinate origin of the pupil center, the vertex normal or the like. The coordinate setting section 112 forms the coordinate system on the basis of the feature signals corresponding to the image of the feature portion of the anterior eye part of the subject eye included in the second received light signal. Besides, the coordinate setting section 112 forms a coordinate system on the basis of the marker signal concerning the marker provided at the subject eye included in the second received light signal and the signal concerning the anterior eye part of the subject eye. The coordinate setting section 112 can determine the coordinate origin and the direction of the coordinate axis on the basis of the second received light signal including the marker signal. The coordinate setting section 112 obtains the coordinate origin on the basis of the marker signal in the second received light signal, obtains the rotation and movement of the coordinate axis on the basis of at least one of the feature signals of the anterior part of the subject eye in the second received light signal, and can correlates the measurement data with the coordinate axis. Alternatively, the coordinate setting section 112 obtains the coordinate origin on the basis of at least one of the feature signals concerning the anterior eye part in the second received light signal, obtains the rotation and movement of the coordinate axis on the basis of the marker signal in the second received light signal, and correlates the measurement data with the coordinate axis. Alternatively, the coordinate setting section 112 obtains the coordinate origin, the rotation and movement of the coordinate axis on the basis of at least one of the feature signals of the anterior eye part of the subject eye in the second received light signal, and correlate the measurement data with the coordinate axis.

One of, some of, or all of the first illumination optical system 10, the first light receiving optical system 20, the second light receiving optical system 30, the common optical system 40, the adjusting optical system 50, the second illumination optical system 70, and the second light sending optical system 80 are suitably put on the alignment section of the optical system 100. The alignment control section 113 can move the alignment section in response to the movement of the subject eye in accordance with the calculation result of the coordinate setting section 112 on the basis of the second received light signal obtained by the second light receiving section. The marker setting section 114 forms the marker related to this coordinate system in the anterior part of the subject eye on the basis of the coordinate system set by the coordinate setting section 112. The input/output section 115 is an interface for outputting data and calculation results such as aberration amount, coordinate origin, coordinate axis, rotation of coordinate axis, and movement thereof, to an operating apparatus. The display section 240 displays the optical characteristics of the subject eye obtained by the measurement section 111 in relation to the coordinate system formed by the coordinate setting section.

An operating apparatus 300 includes an operation control section 121, a working section 122, and a memory section 123. The operation control section 121 controls the working section 122, and controls an operation such as keratectomy. The working section 122 includes a laser for the operation such as keratectomy. The operation memory section 123 stores data for keratectomy, nomogram, and data for operations such as operation plans.

Hereinafter, embodiments of the present invention will be described in detail with reference to the drawings.

1. Explanation of the Principle of an Eye Characteristic Measuring Apparatus

Next, a flowchart concerning the determination of coordinates by the eye characteristic measuring apparatus of the invention will be described.

Figure 5:
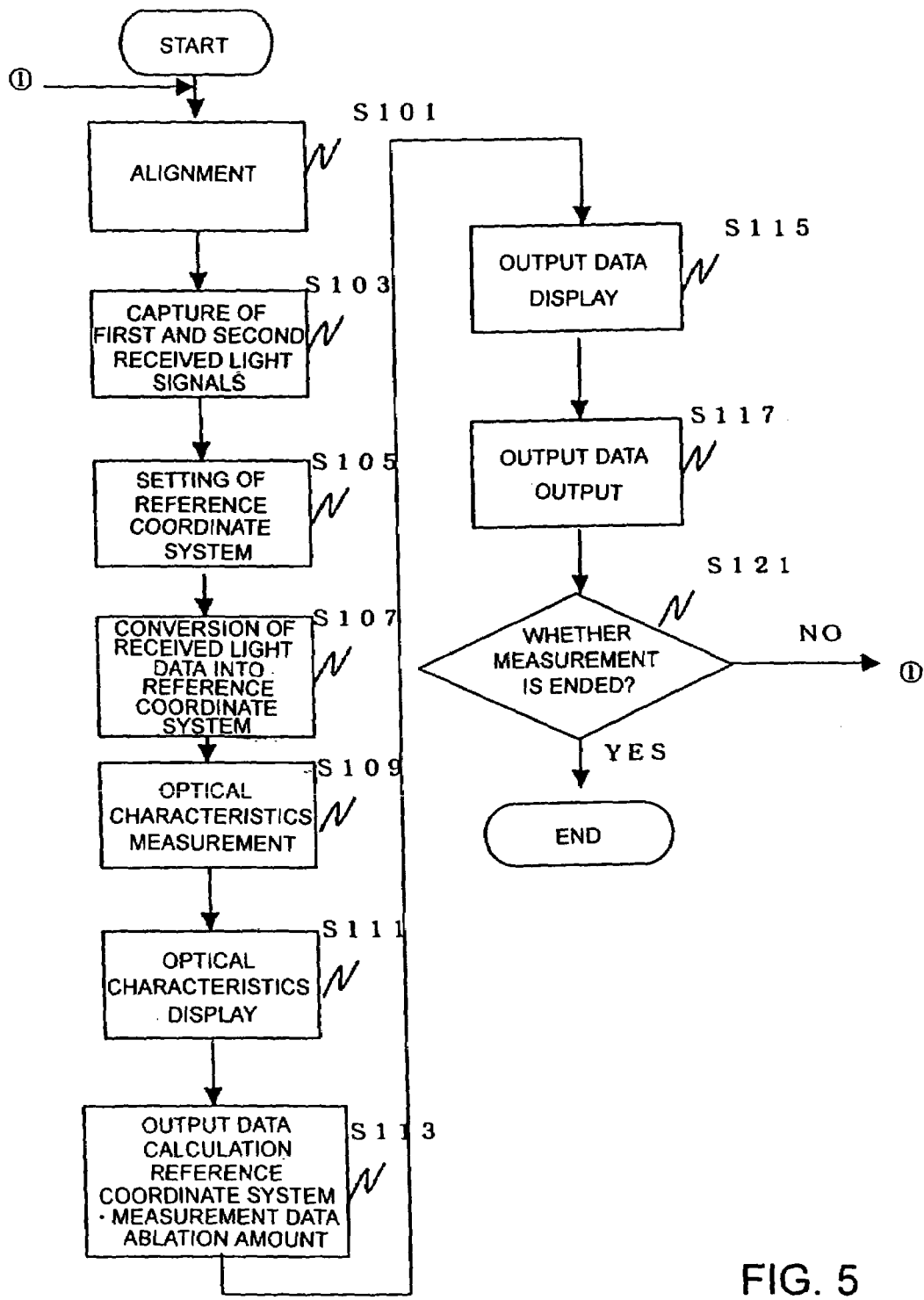
FIG. 5 is a flowchart of a first embodiment showing the operation of the eye characteristic measuring apparatus of the invention.

(1) First Method (Single Measurement) for Determining Coordinates on the Basis of a Feature Portion FIG. 5 is a flowchart of a first embodiment showing the operation of the eye characteristic measuring apparatus of the invention.

Figure 6:
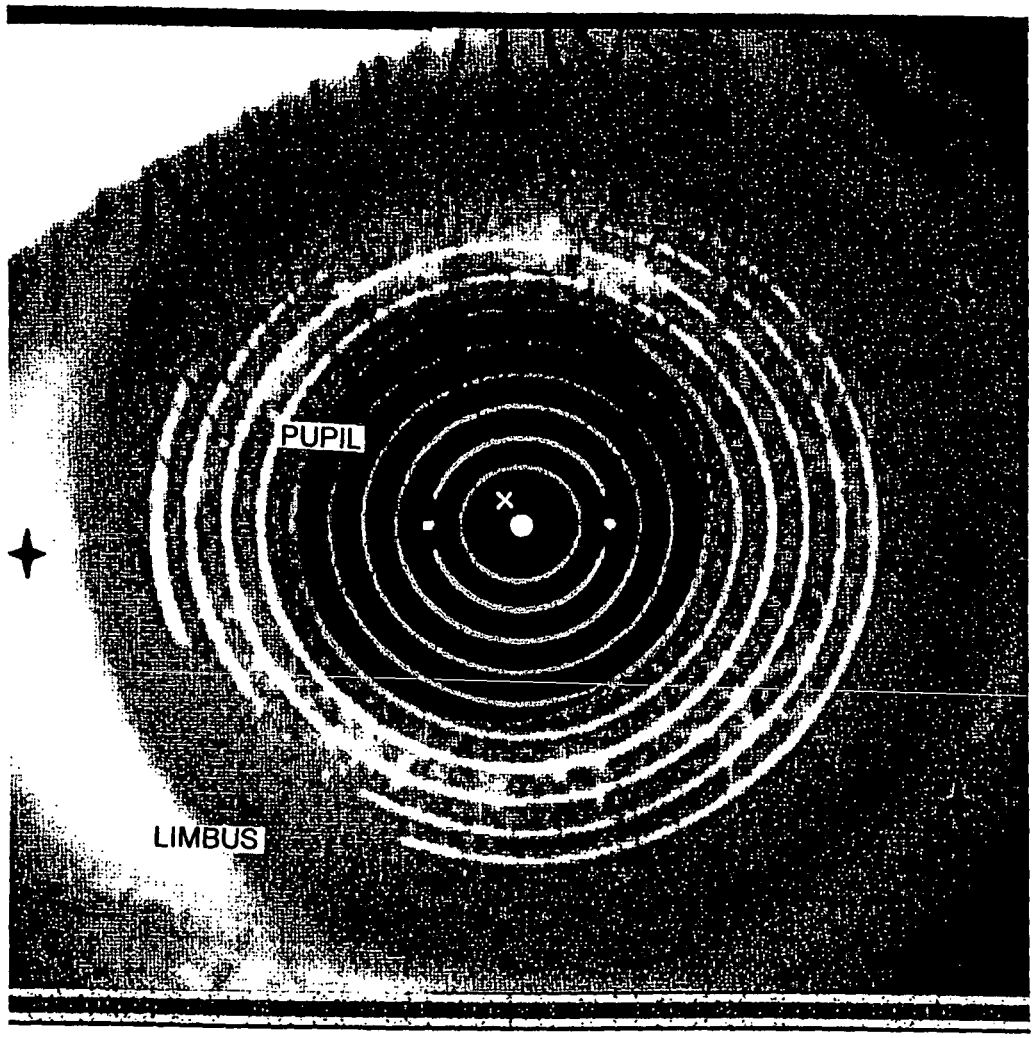
FIG. 6 is an explanatory view of an image of an anterior part of the eye.

First, a signal from the second light receiving section 35 is formed as an image of an anterior eye part on a monitor screen of the display section 230. FIG. 6 is an explanatory view of the image of the anterior eye part. In the drawing, "x" designates a pupil center, "O" designates a cornea vertex (center), and an asterisk mark designates an alignment marker. An actual alignment marker may have a different shape such as a circle. The pupil center is mainly treated as the origin of an operation apparatus. The cornea center is mainly treated as the center of a CCD or a machine. As shown in the drawing, in addition to the image of the placido ring 1, light from the second light source section 31 appears as a bright point in the vicinity of the cornea vertex of the eye to be examined. When the eye characteristic measuring apparatus is aligned in the X-Y directions with respect to the eye to be examined while the image of the anterior eye part of the eye to be examined is observed, alignment in the z direction is also performed by the adjusting optical system 50 (S101).

Next, for example, a first received light signal and a second received light signal appearing in the rings are read (S103). The coordinate origin and the axial directions are determined by using the feature signals included in the second received light signal and indicating the image of the anterior part of the eye to be examined including the feature portion, and a reference coordinate system is set (S105). Here, as the feature portion of the anterior eye part of the eye to be examined, for example, a pupil position, an iris position, an iris pattern, a pupil shape, a limbus shape, a marker formed at the anterior part of the eye to be examined (in case there is a marker), and the like can be named. It is preferable that the reference coordinate system is made the coordinate origin used in the operation apparatus 300, and is obtained from, for example, the pupil position of the eye to be examined, the iris position of the eye to be examined, the pupil shape, the limbus shape, the iris pattern (iris marking) of the eye to be examined, or the like. The pupil center, the cornea center or the like is conceivable as the coordinate origin. In the case where the marker is formed, the coordinate axis can be set by a linear line passing through the marker and the pupil center. In the case where the marker is formed, the coordinate rotation-movement can be measured by, for example, the rotation-movement of the marker.

Figure 7:
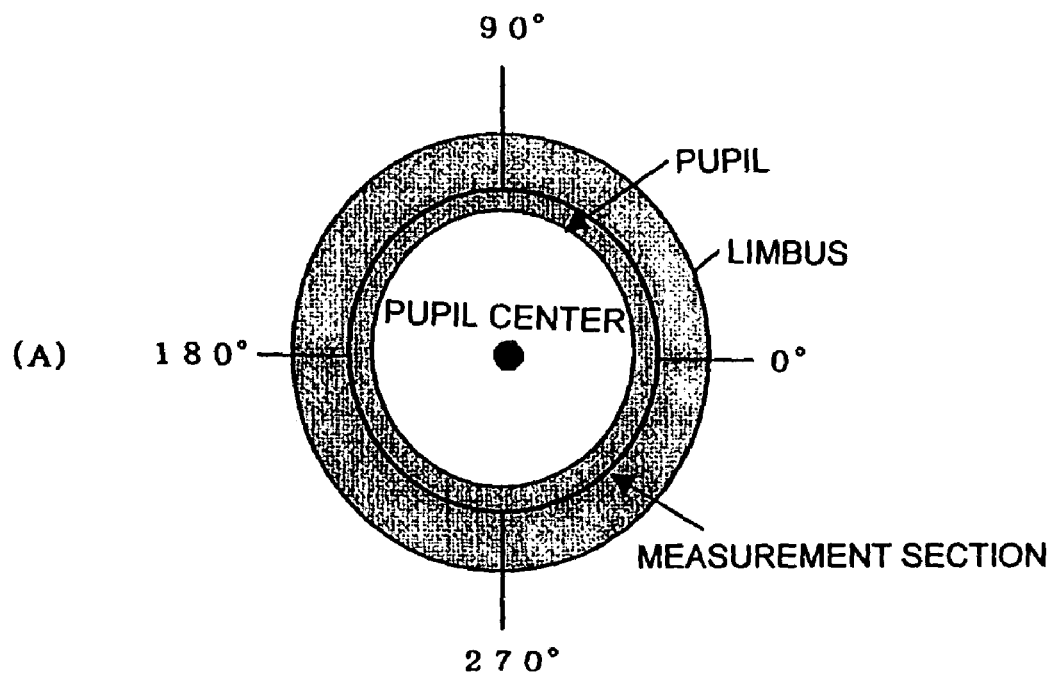
FIG. 7 is an explanatory view relating to measurement of rotation of coordinate axis.
Figure 7:
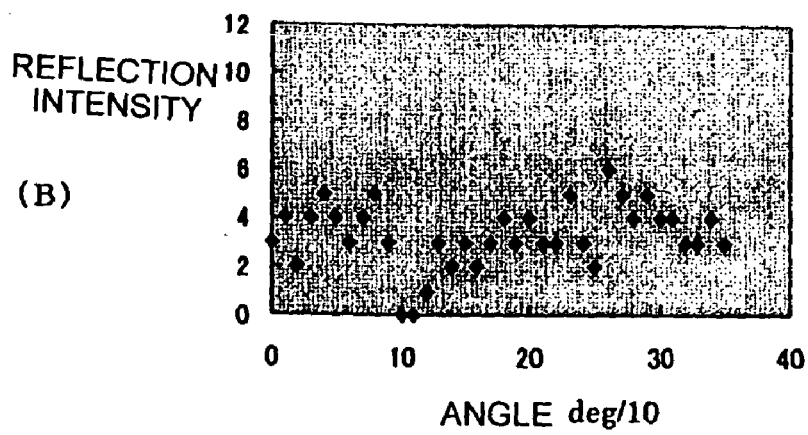

Besides, the coordinate axis and the rotation (cyclo-torsion) can be measured by the pattern of the pupil iris (iris marking) in addition to the marker. Here, FIG. 7 is an explanatory view relating to the measurement of the coordinate axis-rotation. First, as shown in FIG. 7(*a*), for example, the pattern is analyzed by reflection intensity or the like on the rings with the pupil center as the center. Then, as shown in FIG. 7(*b*), the pattern of the reflection intensity with respect to angles is prepared. The coordinate axis can be set by this pattern. Besides, the coordinate rotation can be measured by matching the analyzed pattern on the periphery. That is, when the eye is rotated (cyclo-torsion), a graph of such intensity is laterally shifted by a rotation angle. The amount of the lateral shift can be obtained by an angle at which correlation of the respective measurement values and the reference graph is highest.

Figure 8:
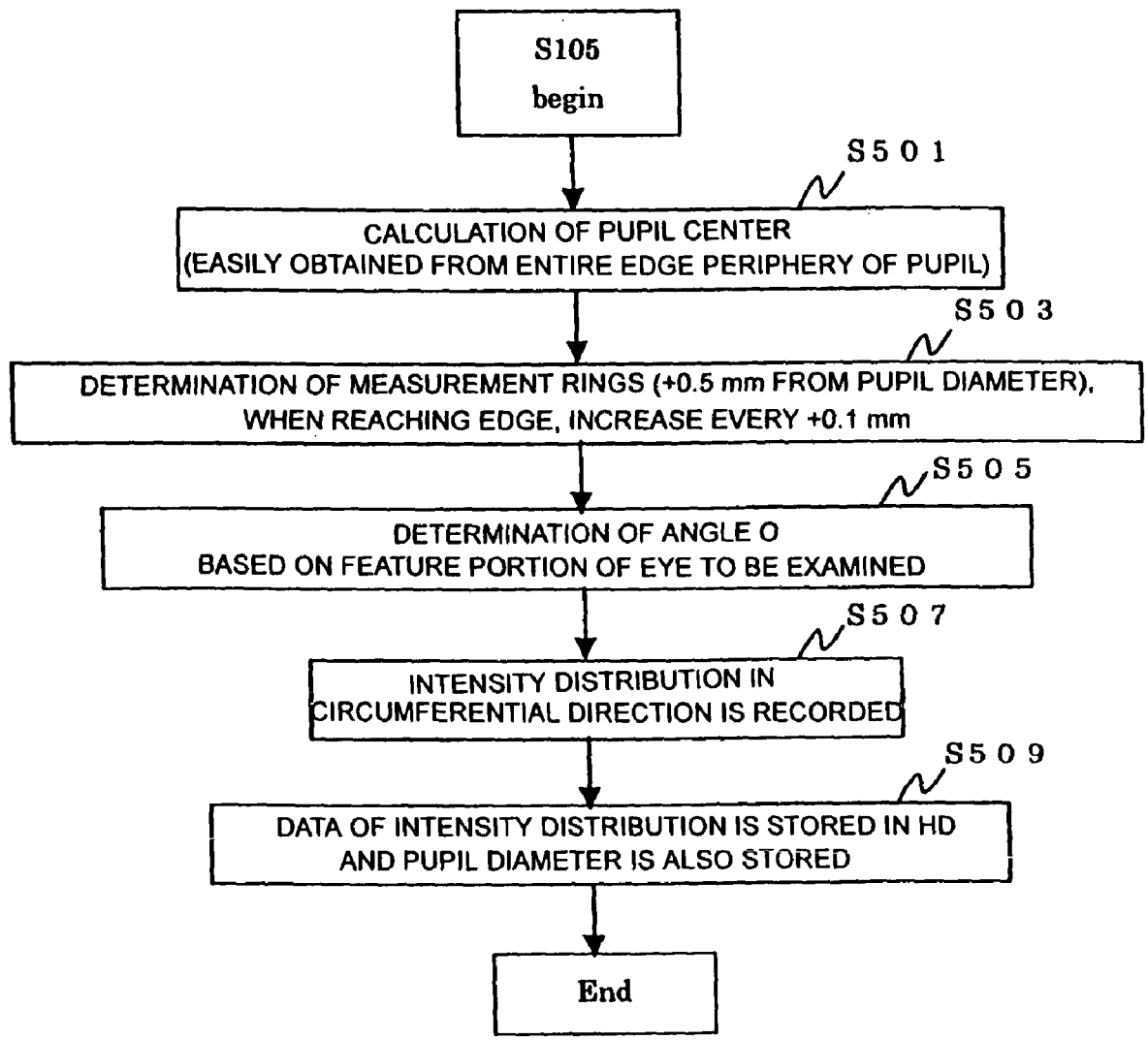
FIG. 8 is a flowchart for setting a reference coordinate system.

FIG. 8 shows a flowchart for setting the reference coordinate system. This is a detailed flowchart of the step S105, and calculation of the pupil center and measurement of the measurement rings are carried out.

First, in order to determine the coordinate origin, the pupil center is calculated (easily obtained from the entire edge periphery of the pupil) (S501). Next, the measurement rings are determined (for example, +0.5 mm from the pupil diameter). When it reaches the edge, it is increased every predetermined length, for example, every +0.1 mm (S503). Next, in order to determine the coordinate axis, an angle is determined on the basis of the feature portion of the eye to be examined (S505). Next, the intensity distribution in the circumferential direction is recorded (S507). Next, data of the intensity distribution is stored in a hard disk (HD) or the like, and the pupil diameter is also stored (S509).

Next, returning to the flowchart of FIG. 5, the received light position data of the light flux having passed through the Hartmann plate 22 as the conversion member is obtained at first in the CCD coordinate system (measurement coordinate system) by the first light receiving section 23, and this is converted into coordinate values in the reference coordinate system (S107). Besides, the optical characteristics are obtained based on the first or the second received light signal (S109). Here, the optical characteristics are, for example, aberration (corneal, internal, ocular) refractive power, cornea shape, and the like. That is, the refractive power of the eye to be examined is obtained based on the first received light signal, and the cornea shape is obtained based on the second received light signal. Next, the measured optical characteristics are displayed (S111). Then, the output data is calculated (S113). As the output data, for example, data of the reference coordinate system, measurement data, an aberration amount itself of the eye to be examined, optical characteristics data, an ablation amount required for surgical removal by the operation apparatus, and the like are obtained by calculation. Next, these output data are displayed (S115). Furthermore, these output data are output as required (S117). Here, an output form includes, for example, following modes.

<1> An offline mode in which an output is made through a recording medium such as a floppy disk or a CD-ROM, or an interface such as a signal line or a wireless line, and then, a surgical operation is carried out at another timing.

<2> A mode in which the output data is connected to the operation apparatus 300 online through an interface such as a signal line, and the optical characteristics of the eye to be examined are measured continuously or by switching at the time of a surgical operation.

As stated above, if the measurement is not to be ended after the data output, it is repeated, and if to be ended, the measurement is ended (S121).

Figure 9:
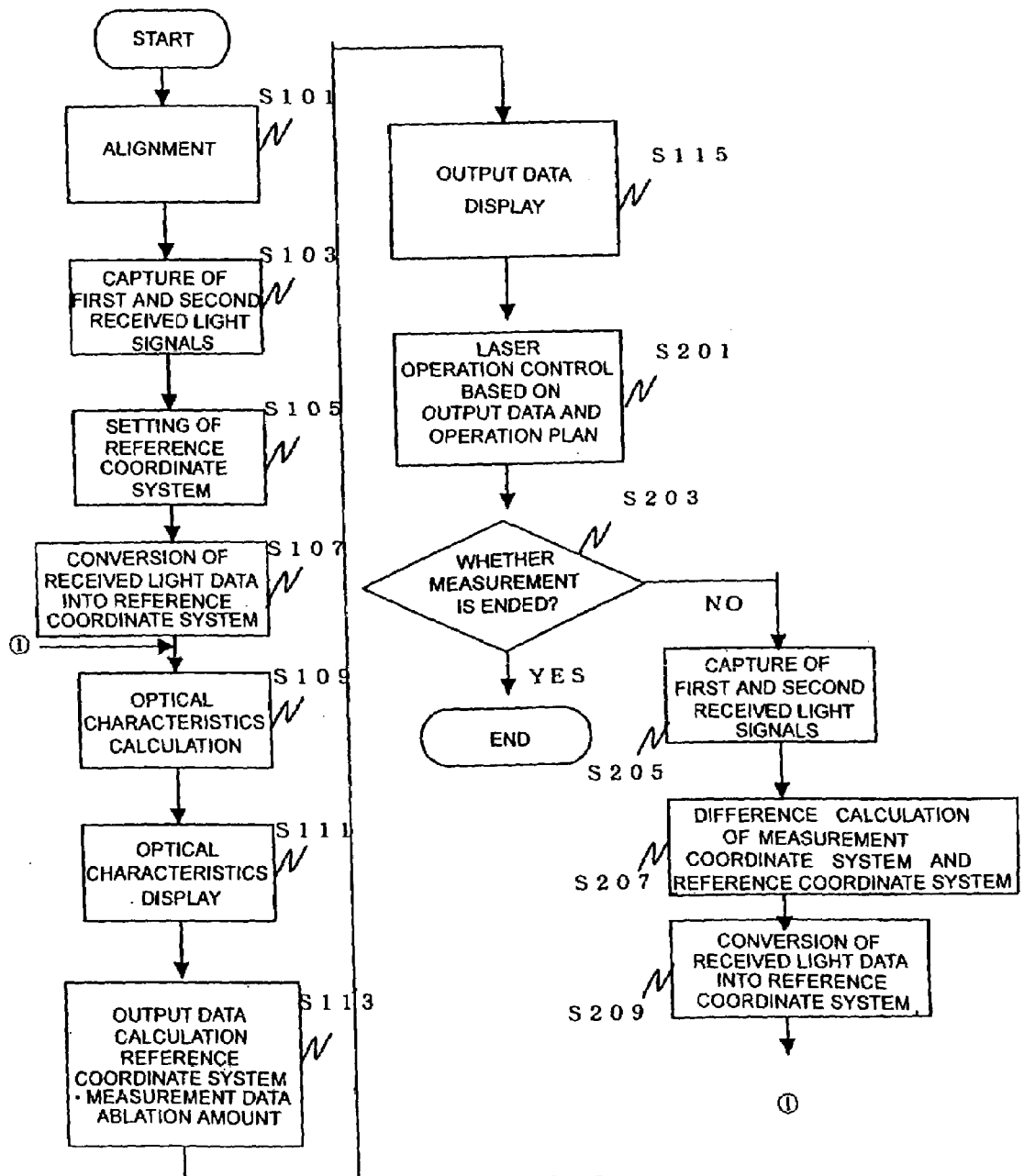
FIG. 9 is a flowchart of a second embodiment showing the operation of the eye characteristic measuring apparatus of the invention.

(2) First Method (Plural Measurements) for Determining Coordinates Based on the Feature Portion FIG. 9 is a flowchart of a second embodiment showing the operation of the eye characteristic measuring apparatus of the invention.

Here, the same portions (S101 to S115) as the first embodiment will be omitted. As stated above, after the output data is displayed (S115), the laser operation apparatus 300 is controlled based on these output data and a surgical operation plan (S201). If the measurement is to be ended after the data output, the measurement is ended, and if the measurement is not to be ended, the procedure proceeds to a next routine (S203). In the case where the measurement is not to be ended, the first and the second received light signals are further captured (S205). Based on these signals, a difference between the measurement coordinate system and the reference coordinate system is calculated and confirmed (S207). In accordance with the calculation results, the received light data is converted into the reference coordinate system (S209). Thereafter, the procedure proceeds to step S111.

Figure 10:
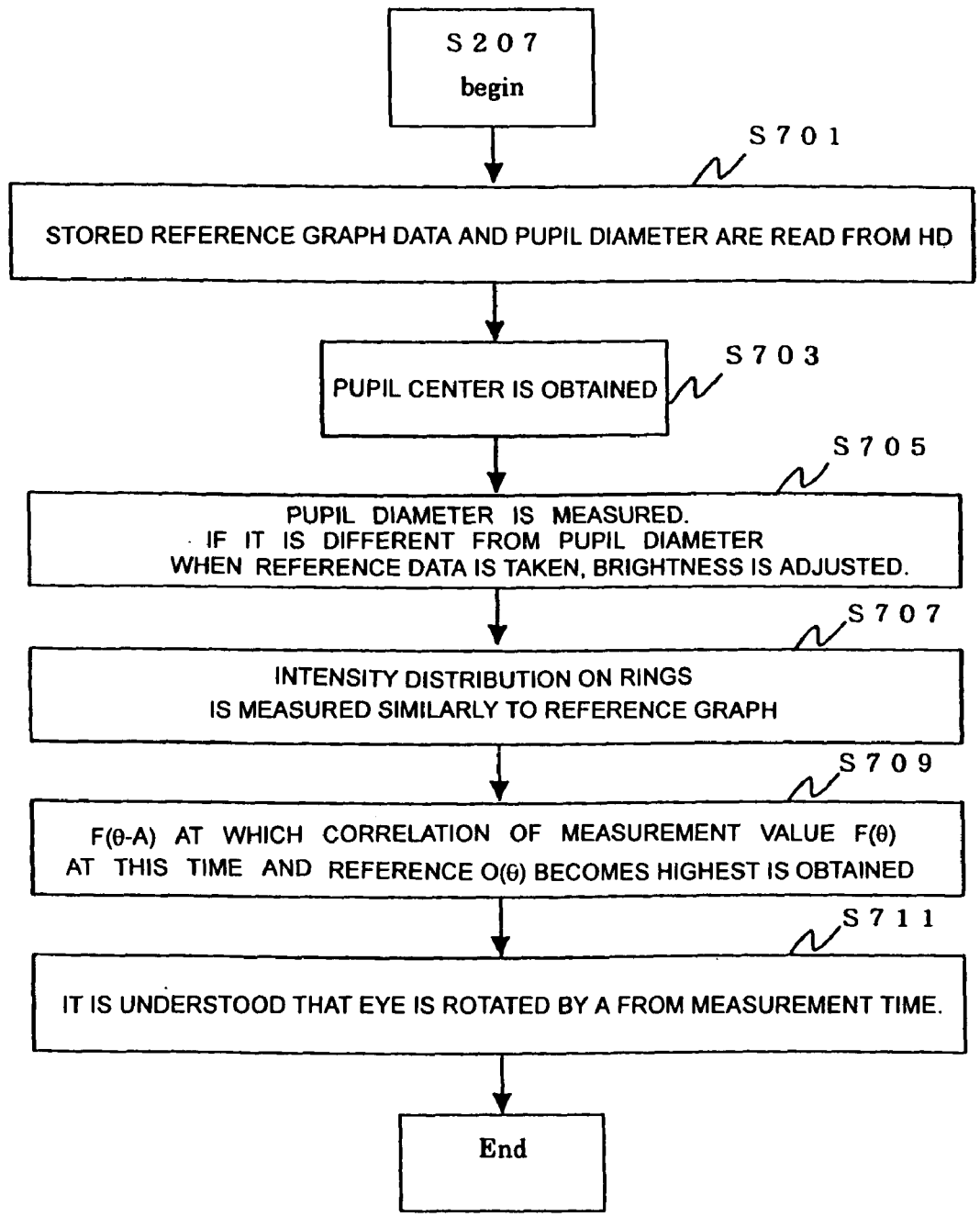
FIG. 10 is a flowchart for confirming a difference between a measurement coordinate system and a reference coordinate system.

Here, FIG. 10 shows a flowchart for confirming the difference between the measurement coordinate system and the reference coordinate system. This is a detailed flowchart of the step S207, and calculation of the pupil center, measurement of measurement rings, and the like are subjected to correlation processing, and a consistent coordinate position is obtained.

First, the stored reference graph data O(θ) and pupil diameter are read in from the memory 240 such as the hard disk (HD) (S701). As the reference graph data O(θ), for example, the intensity distribution on the rings shown in FIG. 7 can be used. Next, the pupil center is obtained based on the read digital (S703). Next, the pupil diameter is measured, and when it is different from the pupil diameter at the time when the reference graph data O(θ) is obtained, the brightness is adjusted (S705). Next, similarly to the reference graph data, the measured graph data F(θ), for example, the intensity distribution on the rings is measured (S707). Next, measured graph data F(θ−A) rotated by an angle A so that the correlation between the graph data F(θ) measured this time and the reference graph data O(θ) becomes highest is obtained (S709). In this way, it is understood that the eye is rotated by the angle A from the measurement time (S711).

Figure 11:
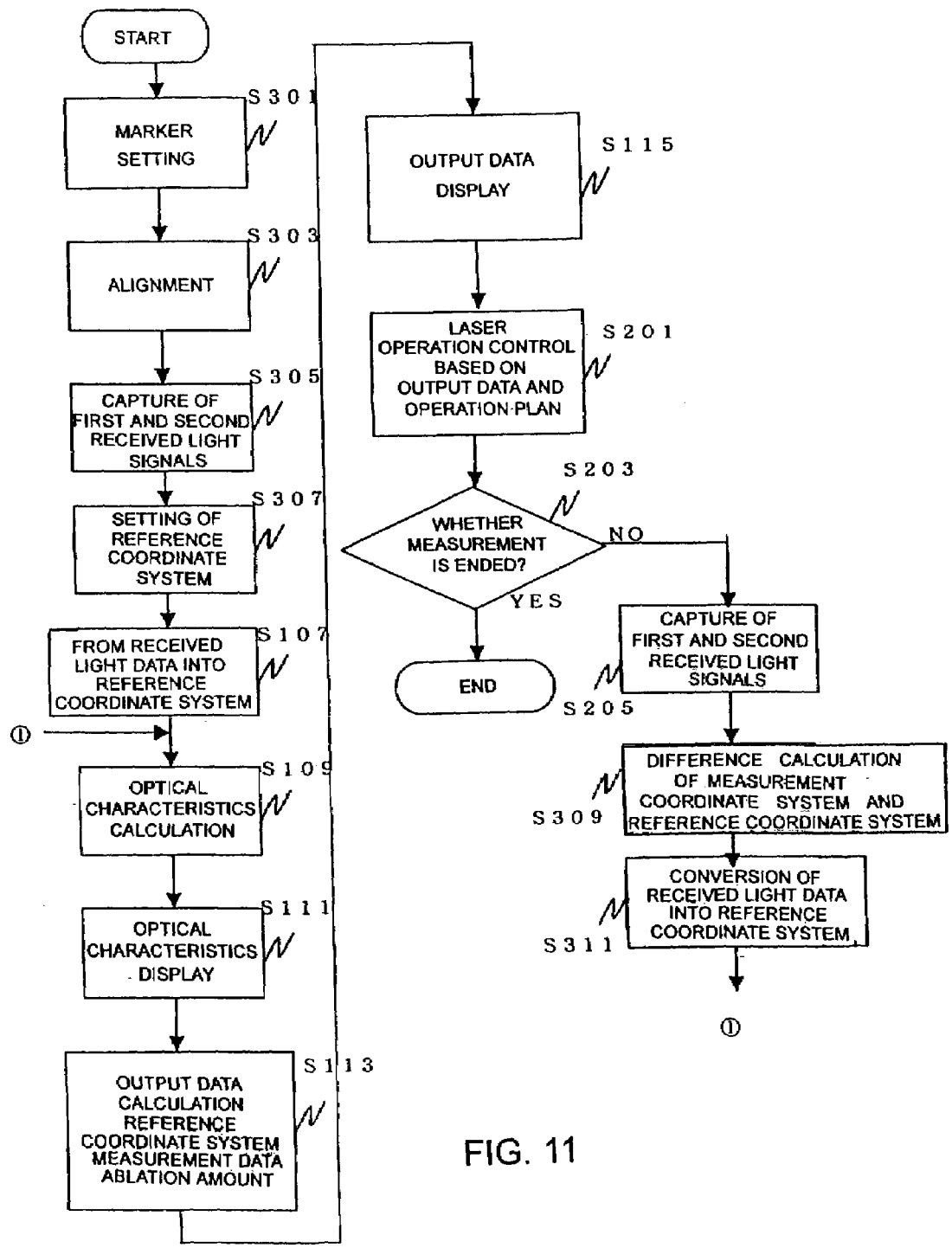
FIG. 11 is a flowchart of a third embodiment showing the operation of the eye characteristic measuring apparatus of the invention.

(3) Second Method for Setting a Coordinate System by using a Marker Formed at the Eye to be Examined FIG. 11 is a flowchart of a third embodiment showing the operation of the eye characteristic measuring apparatus of the invention.

First, a marker is set at the eye to be examined (S301) Here, light from the second light source section 31 appears as a bright point in the vicinity of the cornea vertex of the eye to be examined. While observing the image of the anterior eye part of the eye to be examined and the marker, the eye characteristic measuring apparatus is aligned in the X-Y directions with respect to the eye to be examined (S303). Next, the first received light signal and the second received light signal appearing in the rings are read (S305). The coordinate origin and axial directions are determined by using the feature signals indicating the image of the feature portion of the anterior eye part of the eye to be examined and included in the second received light signal, and the marker provided at the eye to be examined, and the reference coordinate system is set (S307). Incidentally, by setting plural markers, the coordinate origin and the axial directions may be determined from only the markers. Besides, these may be determined from the first received light signal and the marker, or the pupil centers corneal center and the marker or the like.

Subsequent steps S107 to S115, and S201 to S205 are the same as the above. Thereafter, a calculation-confirmation processing (S309) of the difference between the measurement coordinate system and the reference coordinate system, and a processing (S311) for converting the received light data into the reference coordinate system are as described above. However, as the reference graph data and the measurement graph data, in addition to the foregoing intensity distribution, it is possible to use plural markers, or the marker and the pupil center, the corneal center or the first received light signal or the like.

Figure 12:
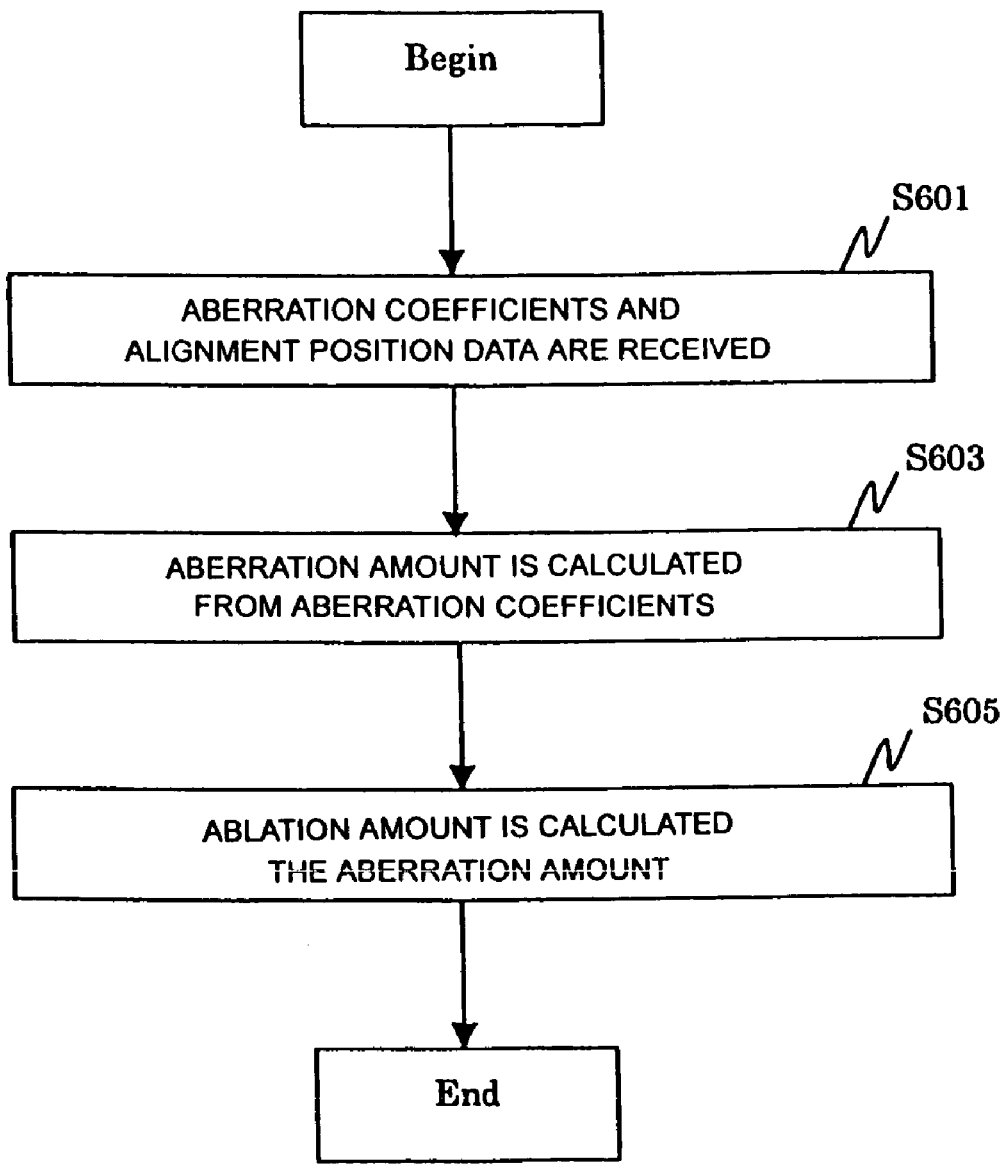
FIG. 12 is a flowchart for obtaining an ablation amount.

Next, FIG. 12 shows a flowchart for obtaining an ablation amount. In general, this processing is executed based on the calculation results of the calculation section 210 by the operation control section 121 in the operation apparatus 300. Alternatively, this processing can be also executed by the calculation section 210 or the like at the side of the eye characteristic measuring apparatus 100, and in that case, the eye characteristic measuring apparatus 100 is further provided with means for inputting or storing data relating to the operation apparatus 300, and the ablation amount obtained by calculation can be transmitted to the operation apparatus 300 through the input/output section 115. As a processing flow, first, aberration coefficients and alignment position data are received (S601). Next, an aberration amount is calculated from the aberration coefficients (S603). Next, the ablation amount is calculated from the aberration amount (S605).

INDUSTRIAL APPLICABILITY

According to the present invention, as described above, it is possible to provide the eye characteristic measuring apparatus in which the measuring apparatus of the eye characteristics, the operation apparatus, and the coordinate origin and coordinate axes of each eye are sufficiently related with one another.

Besides, according to the invention, the relating with the coordinate axes can be performed with respect to rotation-movement of the eye as well. Further, according to the invention, handling is enabled in accordance with motion of the eye.

The invention claimed is:

1. An eye characteristic measuring apparatus, comprising:
a first illumination optical system having a first light source section for emitting a first light flux of a first wavelength, and for illuminating an eyeground of an eye to be examined with the first light flux from the first light source section;
a first light receiving optical system having a first light receiving section for forming a first received light signal from a received light flux, and for guiding a light flux reflected and returned from the eyeground of the eye to be examined to the first light receiving section;
a second light receiving optical system having a second light receiving section for forming a second received light signal including information of an anterior eye part from a received light flux, and for guiding a second light flux including information relating to a feature portion of the anterior eye part of the eye to be examined to the second light receiving section;
a coordinate setting section for forming a coordinate system based on a feature signal included in the second received light signal and corresponding to an image of the feature portion of the anterior eye part of the eye to be examined, and for correlating measurement data obtained based on the first received light signal with the coordinate system;
a measurement section for obtaining optical characteristics including refractive power of the eye to be examined based on coordinate values in the coordinate system, the coordinate values into which the measurement data are obtained based on the first received light signal of the first light receiving section are converted; and
a display section for displaying the optical characteristics of the eye to be examined obtained by the measurement section in relation to the coordinate system formed by the coordinate setting section.

2. An eye characteristic measuring apparatus according to claim 1, wherein the coordinate setting section determines a coordinate origin and a direction of a coordinate axis based on the second received light signal including the feature signal of the anterior eye part of the eye to be examined.

3. An eye characteristic measuring apparatus according to claim 2, wherein the coordinate setting section obtains the coordinate origin, and rotation and movement of the coordinate axis based on at least one of the feature signals of the anterior eye part of the eye to be examined in the second received light signal, and relates measurement data with the coordinate axis.

4. An eye characteristic measuring apparatus according to claim 2, wherein the feature signal includes at least one of a pupil position, a pupil center, a cornea center, an iris position, an iris pattern, a pupil shape, and a limbus shape.

5. An eye characteristic measuring apparatus according to claim 4, further comprising a marker formation section for forming a marker related with the coordinate system at the anterior eye part of the eye to be examined based on the coordinate system set by the coordinate setting section.

6. An eye characteristic measuring apparatus according to claim 1, wherein the measurement section calculates an ablation amount based on an aberration result, and outputs a calculation result to an operation apparatus.

7. An eye characteristic measuring apparatus according to claim 1, further comprising an alignment section having the first light receiving optical section or the second light receiving optical section, wherein
the alignment section can be moved in accordance with motion of the eye to be examined based on the second received light signal obtained by the second light receiving section.

8. An eye characteristic measuring apparatus, comprising:
a first illumination optical system having a first light source section for emitting a first light flux of a first wavelength, and for illuminating an eyeground of an eye to be examined with the first light flux from the first light source section;
a first light receiving optical system having a first light receiving section for forming a first received light signal from a received light flux, and for guiding a light flux reflected and returned from the eyeground of the eye to be examined to the first light receiving section;

a second light receiving optical system having a second light receiving section for forming a second received light signal including information of an anterior eye part from a received light flux, and for guiding a second light flux including information relating to a marker formed at the anterior eye part of the eye to be examined to the second light receiving section;

a coordinate setting section for forming a coordinate system based on a marker signal concerning the marker provided at the eye to be examined, and a feature signal corresponding to an image of a feature portion of the anterior eye part of the eye to be examined, which are included in the second received light signal, and for correlating measurement data obtained based on the first received light signal with the coordinate system;

a measurement section for obtaining optical characteristics including refractive power of the eye to be examined based on coordinate values in the coordinate system, the coordinate values into which the measurement data are obtained based on the first received light signal of the first light receiving section are converted; and a display section for displaying the optical characteristics of the eye to be examined obtained by the measurement section in relation to the coordinate system formed by the coordinate setting section.

9. An eye characteristic measuring apparatus according to claim 8, wherein the coordinate setting section determines a coordinate origin and a direction of a coordinate axis based on the second received light signal including the marker signal.

10. An eye characteristic measuring apparatus according to claim 8, wherein the feature signal includes at least one of a pupil position, a pupil center, a cornea center, an iris position, an iris pattern, a pupil shape, and a limbus shape.

11. An eye characteristic measuring apparatus according to claim 8, wherein the coordinate setting section obtains a coordinate origin based on the marker signal in the second received light signal, obtains rotation and movement of a coordinate axis based on at least one of the feature signals of the anterior eye part of the eye to be examined in the second received light signal, and relates measurement data with the coordinate axis.

12. An eye characteristic measuring apparatus according to claim 8, wherein the coordinate setting section obtains a coordinate origin based on at least one of the feature signals of the anterior eye part in the second received light signal, obtains rotation and movement of a coordinate axis based on the marker signal in the second received light signal, and relates measurement data with the coordinate axis.

13. An eye characteristic measuring apparatus according to claim 8, wherein the coordinate setting section obtains a coordinate origin, and rotation and movement of a coordinate axis based on at least one of the feature signals of the anterior eye part of the eye to be examined in the second received light signal, and relates measurement data with the coordinate axis.

14. An eye characteristic measuring apparatus according to claim 8, wherein the measurement section calculates an ablation amount based on an aberration result, and outputs a calculation result to an operation apparatus.

15. An eye characteristic measuring apparatus according to claim 8, further comprising an alignment section having the first light receiving optical section or the second light receiving optical section, wherein the alignment section can be moved in accordance with motion of the eye to be examined based on the second received light signal obtained by the second light receiving section.

* * * * *